United States Patent
Bruggers

(10) Patent No.: US 10,293,189 B2
(45) Date of Patent: May 21, 2019

(54) ULTRASONIC APPARATUS, A THERAPEUTIC SYSTEM AND A METHOD OF INCREASING A WORKFLOW

(75) Inventor: Jan Willem Bruggers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1450 days.

(21) Appl. No.: 12/527,632

(22) PCT Filed: Feb. 18, 2008

(86) PCT No.: PCT/IB2008/050574
§ 371 (c)(1),
(2), (4) Date: Aug. 18, 2009

(87) PCT Pub. No.: WO2008/102293
PCT Pub. Date: Aug. 28, 2008

(65) Prior Publication Data
US 2010/0056914 A1    Mar. 4, 2010

(30) Foreign Application Priority Data
Feb. 23, 2007   (EP) .................................... 07102933

(51) Int. Cl.
*A61B 8/00* (2006.01)
*A61N 7/02* (2006.01)
(Continued)

(52) U.S. Cl.
CPC .............. *A61N 7/02* (2013.01); *A61B 5/0035* (2013.01); *A61B 5/055* (2013.01); *A61B 90/50* (2016.02);
(Continued)

(58) Field of Classification Search
CPC .. A61B 2017/00907; A61B 2017/2253; A61B 5/0035; A61B 5/055; A61N 7/02
(Continued)

(56) References Cited

U.S. PATENT DOCUMENTS 4,233,988 A * 11/1980 Dick .................... A61B 8/0825
128/915
4,298,009 A * 11/1981 Mezrich ............... A61B 8/0825
128/915
(Continued)

FOREIGN PATENT DOCUMENTS

| JP | 2002238898 A | 8/2002 |
| WO | 2006136912 A1 | 12/2006 |
| WO | 2007035529 A2 | 3/2007 |

OTHER PUBLICATIONS

Smith et al, Control system for an MRI compatible intracavitary ultrasound array, for thermal treatment of prostate disease, Int. J. Hyperthermia, vol. 17, No. 3, 2001, pp. 271-282.*
(Continued)

*Primary Examiner* — Rajeev P Siripurapu

(57) ABSTRACT

An ultrasonic apparatus (10) includes a support (2) for accommodating a portion of a patient (14). The support includes a first reservoir (8) with a transmission medium. The support further includes an ultrasonic wave source (9) having an emitting surface (7) being conceived to be oriented towards the portion of the patient (14) in use. The ultrasonic apparatus further includes a substantially transparent aperture (26) arranged in the support (2) for enabling an inspection of the first reservoir. A therapeutic system increases a workflow of the ultrasonic apparatus.

7 Claims, 3 Drawing Sheets

(51) Int. Cl.
*A61B 5/00* (2006.01)
*A61B 5/055* (2006.01)
*A61B 17/00* (2006.01)
*A61B 17/225* (2006.01)
*G01R 33/48* (2006.01)
*A61B 90/50* (2016.01)
*A61B 90/00* (2016.01)

(52) U.S. Cl.
CPC ............. *A61B 2017/00907* (2013.01); *A61B 2017/2253* (2013.01); *A61B 2090/374* (2016.02); *A61B 2090/378* (2016.02); *G01R 33/4804* (2013.01); *G01R 33/4814* (2013.01)

(58) Field of Classification Search
USPC ..................................................... 600/411
See application file for complete search history.

(56) References Cited

U.S. PATENT DOCUMENTS

| | | | |
|---|---|---|---|
| 4,646,756 A | | 3/1987 | Watmough et al. |
| 4,932,414 A | | 6/1990 | Coleman et al. |
| 5,158,536 A | * | 10/1992 | Sekins ............... A61F 7/123 128/898 |
| 5,391,197 A | * | 2/1995 | Burdette et al. ............... 601/3 |
| 5,443,068 A | * | 8/1995 | Cline ............... A61B 5/0555 600/411 |
| 6,128,523 A | * | 10/2000 | Bechtold et al. ............. 600/411 |
| 6,216,294 B1 | | 4/2001 | Wess |
| 6,508,774 B1 | | 1/2003 | Acker et al. |
| 7,699,783 B2 | | 4/2010 | Hanover et al. |
| 9,131,919 B2 | | 9/2015 | Summers et al. |
| 2003/0083597 A1 | | 5/2003 | Vitek et al. |
| 2003/0233045 A1 | | 12/2003 | Vaezy et al. |
| 2005/0113692 A1 | | 5/2005 | He et al. |
| 2007/0016039 A1 | | 1/2007 | Vortman et al. |
| 2008/0269607 A1 | | 10/2008 | Ishida et al. |
| 2010/0056914 A1 | | 3/2010 | Bruggers |

OTHER PUBLICATIONS sld.cu, Chapter 7 Therepautic Modalities, http://www.sld.cu/galerias/pdf/sitios/rehabilitacion/sample_chapter_7therapeutic_modalities.pdf, Jul. 2004, pp. 163-190.*

Rewcastle, J. C.; High Intensity Focused Ultrasound for Prostate Cancer: 2006 Technology and Outcome Update; Dept. of Radiology, University of Calgary, Canada.

* cited by examiner

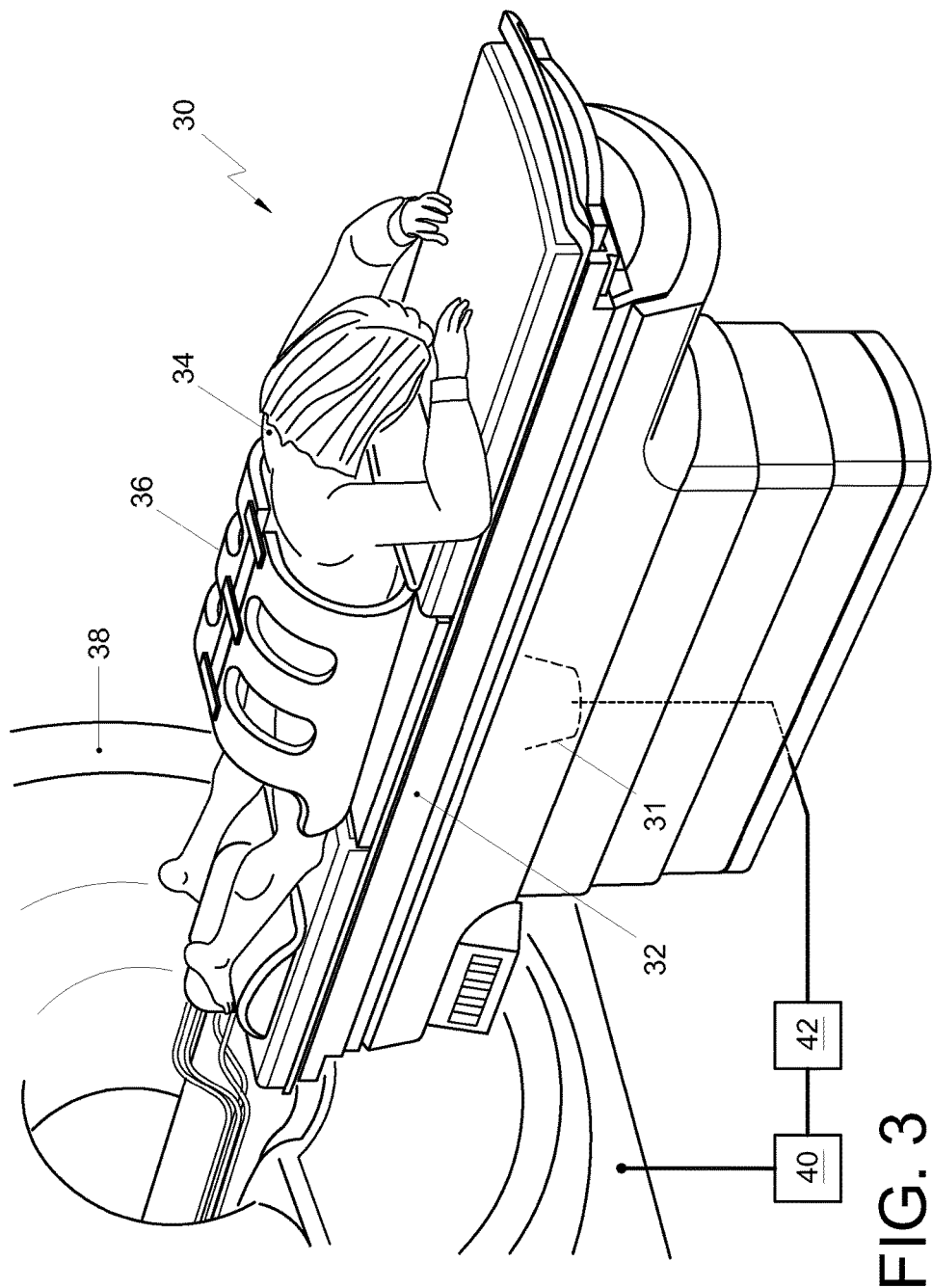

ULTRASONIC APPARATUS, A THERAPEUTIC SYSTEM AND A METHOD OF INCREASING A WORKFLOW

FIELD OF THE INVENTION

The invention relates to an ultrasonic apparatus comprising:
- a support means for accommodating a portion of a patient, said support means comprising a first reservoir for a transmission medium,
- an ultrasonic wave source having an emitting surface being conceived to be oriented towards the portion of the patient in use.

The invention further relates to a therapeutic system comprising the ultrasonic apparatus.

The invention still further relates to a method of increasing a workflow of an ultrasonic apparatus.

BACKGROUND OF THE INVENTION

The ultrasonic apparatus as is set forth in the opening paragraph is known from U.S. Pat. No. 6,508,774 B1. The known apparatus comprises a patient accommodation means, notably a patient support means, in the form of a patient support table on which a patient to be treated is to be positioned. The known apparatus is suitable for carrying out therapeutic procedures by means of application of high energy ultrasonic waves. For this purpose the known apparatus comprises a first reservoir with a transmission medium for supporting a portion of a patient. In the known apparatus deaerated water is used for the transmission medium for conducting the ultrasonic waves substantially without dissipation to the portion of the patient. The support means of the known apparatus further comprises an ultrasonic wave source disposed in the first reservoir and having an emitting surface oriented towards the portion of the patient. In order to couple the ultrasonic waves emanating from the first reservoir to the patient the known ultrasonic apparatus further comprises a second reservoir comprising a coupling medium (gel) providing a low reflectivity interface and having a contact surface with the portion of the patient. During use, the second reservoir is positioned between the first reservoir and the portion of the patient.

In an alternative embodiment of a known high energy focused ultrasonic treatment, a portion of a patient, notably a breast, may be disposed in the first reservoir. In this case the portion of the patient, notably the breast, may be arranged with a second reservoir filled with a coupling medium, the said second reservoir being arranged around the portion of the patient, for example like a wearable.

It is acknowledged in the art that air bubbles may occur at various contact surfaces or within the transmission medium present on the first reservoir. Such contact surfaces may be formed in different circumstances. For example, a suitable contact surface may be formed between the transmission medium present in the first reservoir and the portion of the patient. It is noted that it is possible that the portion of the patient is disposed in the first reservoir, or that the portion of the patient if supported by the first reservoir. The first situation may correspond to a treatment of a substantially isolated part, like a female breast, whereas the second situation corresponds to a conventional, notably abdominal, treatment. Additionally, it is possible that a second reservoir comprising a suitable coupling medium is provided between the transmission medium of the first reservoir and portion of the patient. In this case air bubbles may occur also at a contact surface between the transmission medium and the second reservoir and/or between the first reservoir and the second reservoir.

Also, the air bubbles may occur in the transmission medium, notably due to cavitation processes. It is acknowledged that any air bubble present on a path of an ultrasonic wave substantially deteriorate the therapeutic effect of the treatment, notably high intensity ultrasonic treatment. Moreover, air inclusions in the area of the contact surface, between the second reservoir and the patient may cause severe burns to the patient skin. It is a general practice to reposition the patient, frequently several times, in order to control the air-free interface between the second reservoir and the patient, because presence of air bubbles may distort an ultrasonic field resulting in erroneous treatment.

It is a disadvantage of the known apparatus in that sufficient time is lost due to repositioning of the patient on one hand, and in that the outcome of the treatment may be dependent upon the confidence level with respect to the absence of any air bubbles at the contact surface.

SUMMARY OF THE INVENTION

It is an object of the invention to provide an ultrasonic apparatus wherein the quality of the delivery of ultrasonic waves to the patient is improved and wherein the workflow of the ultrasonic apparatus is increased.

To this end in the ultrasonic apparatus according to the invention the patient support means is arranged with a substantially transparent aperture conceived for enabling a inspection of the first reservoir.

The technical measure of the invention is based on the insight that by providing a visual access to the first reservoir the presence of air inclusions in the first reservoir can easily be detected prior to any clinical procedure, thereby considerably increasing the patient throughput and accuracy of the procedure. It is possible that the first reservoir is arranged for receiving the portion of a patient, notably a breast, the aperture being arranged for enabling the inspection of an area at least around the portion of the patient, notably the breast. It is further possible that apparatus further comprises a second reservoir conceived to be filled with a coupling medium, the aperture being further arranged for enabling inspection of a contact surface at least between the first reservoir and the second reservoir. For some particular treatment procedures, it may be required that the portion of the patient, notably an isolated organ, like a breast, must be positioned in the first reservoir being fitted in a second reservoir filled with a coupling medium. In this case air bubbles may occur on a contact area between the transmission medium and the breast fitted in the second reservoir. It is also possible that a portion of a patient is supported by a suitable supporting surface of the first reservoir, the second reservoir being filled with a coupling medium being disposed between the supporting surface and the portion of the patient. In this case air bubbles may occur at a contact surface between the first reservoir and the second reservoir and between the second reservoir and the portion of the patient. A dimension of the aperture may be suitably chosen. Preferably, a dimension of the aperture is selected around 50-1000 mm$^2$. The sizes of the aperture of 50-200 mm$^2$ are particularly suitable for supporting remote inspection using camera's or optical fibers attached to the aperture.

In an embodiment of the apparatus according to the invention the first reservoir is manufactured from a substantially transparent material, the aperture constituting a wall of the first reservoir.

It has been found to be particularly advantageous to provide a substantially completely transparent first reservoir, as it increases a spatial angle of enabled inspection. Any transparent material, notably a plastic material is suitable for this purpose. This particular embodiment has an additional advantage in case the ultrasonic wave source is disposed in the first reservoir, as the inspector may easily choose a position so that no obstruction of a viewing direction occurs by the volume of the source.

It is noted that use of a window in a patient support table is known from U.S. Pat. No. 6,216,294 B1. The known apparatus is arranged to perform X-ray diagnosis of a patient, wherein the source of the X-rays is disposed in the patient support table. The known arrangement may further comprise a carrier foil arranged on the table top with support cushions filled with water. In case when the known apparatus is used for performing ultrasonic diagnosis or ultrasonic treatment, the ultrasonic apparatus is positioned next to the patient support table and the ultrasonic waves are conducted into the body of the patient through the cushions. When the known apparatus is used for performing lithotrity, the therapy waves can be irradiated through the foil or through a window in the table top into the patient's body. It is noted that the window described with the reference to the known patient support table is not suited to check the presence of air bubbles, as the known window is not suitable to enable visual inspection of the presence of air bubbles in the interface between the patient's skin and the water-filled cushion.

In an embodiment of the apparatus according to the invention the ultrasonic wave source is arranged for performing a high intensity focused ultrasound treatment.

In high intensity focused ultrasound (HIFU) the ultrasound generated by the transducer is focused into a small focal volume at the specific target locations. During a treatment, the beam of focused ultrasound energy penetrates through soft tissue of the patient and causes localized high temperatures (55° to 70° C.) for a few seconds producing well defined regions of protein denaturation, irreversible cell damage, and coagulative necrosis. A single exposure of focused ultrasound energy is called a "sonication." Multiple sonications are necessary to ablate the targeted tissue. Accurate focusing of the ultrasonic beam emanating from the ultrasonic source is designed to limit the ablation to the targeted location.

In a further embodiment of the apparatus according to the invention the apparatus further comprises a diagnostic ultrasonic transducer for enabling targeting of the high intensity focused ultrasound treatment.

Applying HIFU power to a patient's lesion needs planning, targeting the ultrasonic beam and monitoring of the energy delivery. For many application, for example, for prostate ablation, this is done using a diagnostic ultrasonic beam in combination with the HIFU beam. Whereas this diagnostic ultrasound provides some anatomical details and assists with procedure planning and targeting, it does not provide means of measuring the temperature increase generated by HIFU.

The therapeutic system according to the invention comprises an apparatus according as is set forth in the foregoing and a magnetic resonance imaging apparatus arranged for measuring a temperature distribution in the patient.

The technical measure of the invention is based on a further insight that only MR imaging can provide a non-invasive way of measuring the temperature increase in the lesion inside the patient. MR-guided focused ultrasound (HIFU) can provide real-time temperature mapping in multiple planes or 3D, control via real-time feedback the localization of the focal point, and immediately control and assess the ablative effect. Recent advances in MR temperature mapping make it possible to achieve temperature accuracy of 2-3° C. in moving tissue like liver, and 1° C. in stationary tissue. The operation of the magnetic resonance imaging unit for temperature mapping is known per se in the art and will not be explained here in detail.

A method according to the invention for increasing a workflow of an ultrasonic apparatus comprising
  providing a support means (2) comprising a first reservoir (8) with a transmission medium for accommodating a portion of a patient;
  providing an ultrasonic wave source (9) having an emitting surface being oriented towards the portion of the patient;
  positioning a patient on the support means (2);
  inspecting at least the first reservoir using a substantially transparent aperture (26) arranged in the support means (2).

When treating a patient with ultrasound, no air bubbles are allowed between patient and transducer. These air bubbles will otherwise distort this sound bundle and disturb the spot. Conventionally, for enabling high intensity focused ultrasound treatment, the transducer is placed in a water reservoir, disposed in the patient support table. The water reservoir is closed by a membrane. On top of this membrane a gel pad in another water reservoir is placed.

In an embodiment of the method according to the invention, the patient lies in a prone position on top of the gel pad. The water ensures that no air inclusions between gel pad and membrane and gel pad and patient occur. In usual practice this cannot be checked visually. One way for checking the presence of air inclusions on the interface between the gel pad and the patient's skin is by means of acoustic sensors, however, this is time consuming. When there is air between patient and transducer, the patient will have to be unfastened and replaced on the treatment table. This may have to be done several times leading to a substantial time loss.

In accordance with the technical measure of the invention the treatment can be shortened considerably, because the aperture, for example, in the form of a transparent window makes it a lot easier to check whether there is air between gel pad and the patient. Moreover, a lot of time is saved since the patient doesn't need to be unfastened and replaced on the treatment table. This can save approximately 30 minutes or more.

BRIEF DESCRIPTION OF THE DRAWINGS

These and other aspects of the invention will be explained in more detail with reference to figures.

FIG. 3 presents a schematic view of an embodiment of a system according to the invention.

FIGURE DESCRIPTION

Figure 1:
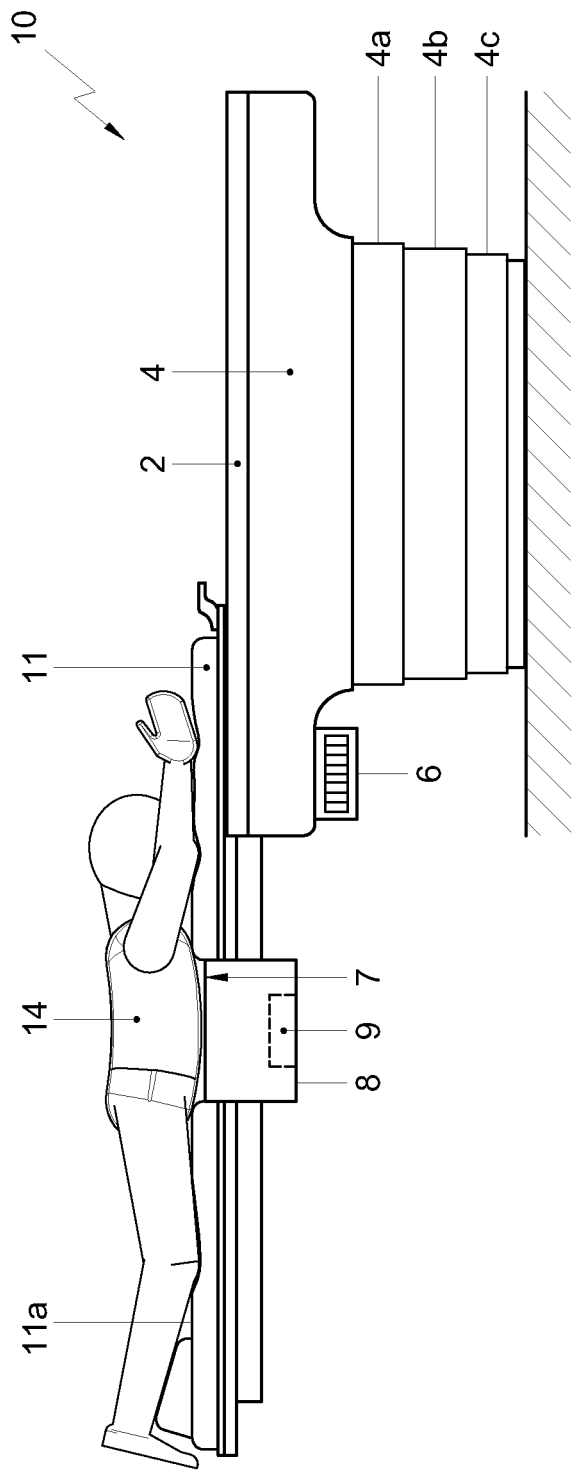
FIG. 1 presents a schematic view of an embodiment of an ultrasonic apparatus according to the state of the art.

FIG. 1 presents a schematic view of an embodiment of an ultrasonic apparatus according to the state of the art. The ultrasonic apparatus 10 comprises a patient support table 2 arranged on a retractable pedestal 4 comprising telescopic portions 4*a*, 4*b*, 4*c*. The patient support table 2 can be controlled using a control means 6, usually comprising touch-sensitive buttons. The ultrasonic apparatus 10 further comprises a source of ultrasonic waves 9 disposed in a first reservoir comprising transmission medium for conducting the ultrasonic waves from the ultrasonic source 9 to the patient 14. Usually, deaerated water is selected for the transmission medium of the first reservoir. The first reservoir is terminated by a membrane 7 which is flexible in order to substantially conform to a portion (not shown) of the patient 14 conceived to be positioned on the apparatus 10 for treatment. In order to couple the ultrasonic waves emanating from the emitting surface 7 a gel pad 11 is provided between the patient 14 and the surface 7. The gel pad serves as a low reflection interface for conducting the ultrasonic waves into the patient. The contact surface 11a of the gel pad 11 and the patient 14 should be kept as much a s possible free from air bubbles. In order to do so, the patient 14 frequently has to be repositioned on the gel pad 11, reducing the time efficiency of the medical procedure.

Figure 2:
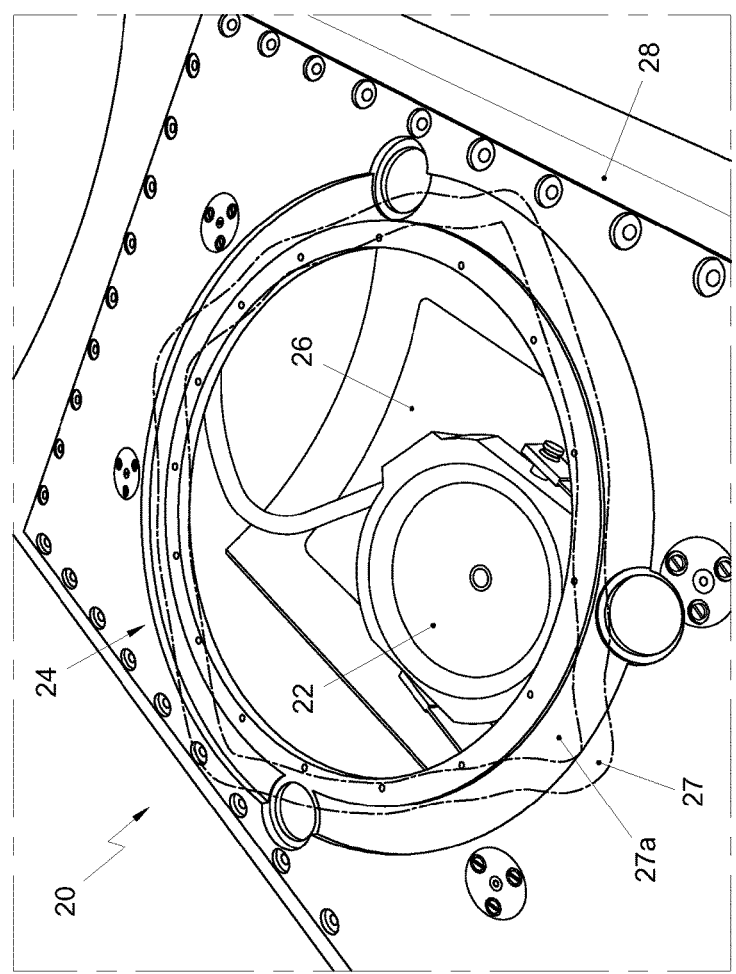
FIG. 2 presents a schematic view of an embodiment of an ultrasonic apparatus according to the invention.

FIG. 2 presents a schematic view of an embodiment of an ultrasonic apparatus according to the invention. FIG. 2 presents a top view on the ultrasonic apparatus 20. The ultrasonic apparatus 20 according to the invention comprises a patient support means 28 wherein a first reservoir 24, filled with a suitable transmission liquid, for example, water, is positioned. For reasons of clarity, the membrane sealing the first reservoir 24 is not shown. The first reservoir 24 comprises a source of ultrasonic waves 22, which is preferably arranged to emit high intensity focused ultrasonic beam. The technique to emit high intensity focused ultrasonic beam is per se known in the art and will not be explained here in detail. In order to couple the ultrasonic beam emanating from the first reservoir to the patient (not shown) a second reservoir 27 comprising a low reflective medium is positioned on the first reservoir 24. Preferably, a suitable gel pad is used for the second reservoir. The second reservoir 27 comprises a contact surface 27a onto which a patient to be treated is positioned. The ultrasonic apparatus 20 according to the invention further comprises an aperture 26 arranged to enable an inspection, for example, a visual inspection, of the contact surface 27a between the second reservoir 27 and the patient (not shown). The aperture 26 is preferably arranged as a substantially transparent window where through medical personnel directly, or using a mirror or a suitable arranged camera, can inspect whether there is no air bubbles between the contact surface 27a and the patient. In case when an air bubble is detected, the patient is repositioned until no air bubbles are present. After that, the patient is suitably immobilized and a treatment may be commenced. It is an advantage of the ultrasound apparatus according to the invention in that a possible presence of air bubbles can be detected and avoided prior to treatment, wherein the patient is to be repositioned only once. Due to this, the time spent on the procedure is substantially decreased and the efficacy of the medical treatment is increased, in particular due to a high confidence level about absence of air inclusions at the interface between the second reservoir 27 and the patient.

FIG. 3 presents a schematic view of an embodiment of a system according to the invention. The system 30 comprises an ultrasonic apparatus 32, discussed in detail with reference to FIG. 2, and an magnetic resonance imaging apparatus 38. The magnetic resonance imaging apparatus is preferably arranged to determine real-time temperature distribution in the patient during the course of high intensity focused ultrasound treatment. The high intensity focused ultrasonic treatment is conducted using the ultrasonic source 31 disposed in a reservoir (not shown) filled with a suitable transmission liquid. For purposes of real-time temperature measurements the patient 34 is provided with a receiving RF antenna 36 for detecting radiofrequency signals emanating from the body of the patient in response to magnetic resonance imaging signals. The technique of temperature mapping using the magnetic resonance imaging apparatus is known per se. The system 30 further comprises a feed-back unit 40 arranged to control a delivery of high intensity ultrasonic waves from the source 31. For this purpose the feed-back unit communicates suitable signals to the control means 42 arranged for steering the ultrasonic source 31. In this way the system 30 operates in a fully automatic mode wherein the real-time data on temperature distribution in a target volume in the patient is used to control the ultrasonic source delivering the treatment. Accordingly, the duration, the targeting and the temperature distribution within the target volume and outside it can be controlled. Preferably, the ultrasonic source 31 comprises a plurality of transducers, each of which can be controlled individually. In this case, based on the real-time temperature distribution in the target volume and outside it, it is possible to modulate the source 31 thereby conforming, for example, a 95% isotherm to the shape of the target volume and avoiding elevated temperatures in critical organs, which may be located nearby.

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below.

The invention claimed is:

1. A method of increasing a workflow of an ultrasonic apparatus, the method comprising:
   providing an ultrasonic apparatus comprising a first reservoir filled with a transmission medium and closed on one face by a contact surface;
   positioning a gel pad between the contact surface and a portion of the patient to receive ultrasound treatment;
   with a camera, inspecting at least the contact surface for bubbles;
   in response to the inspection finding an absence of bubbles, treating the portion of the patient with an ultrasound beam directed from an ultrasound transducer directed through the transmission medium and the gel pad to the portion of the patient and, in response to the inspection finding bubbles, eliminating the bubbles before treating the portion of the patient.

2. The method according to claim 1, wherein the inspecting includes inspecting an area around the portion of the patient to receive the ultrasound treatment.

3. The method according to claim 1, further including:
   wherein the inspecting includes inspecting for bubbles between the first reservoir and the gel pad and in response to finding bubbles, repositioning the portion of the patient and the gel pad.

4. The method according to claim 1, further including:
   with a magnetic resonance device, measuring a temperature distribution in the portion of the patient;
   controlling the ultrasound transducer based on the measured temperature distribution.

5. An ultrasonic apparatus comprising:
   an ultrasonic transducer configured to produce ultrasonic waves;
   a first reservoir containing a transmission medium configured to conduct the ultrasonic waves toward a portion of a patient to be treated;

a flexible membrane connected to the first reservoir disposed between the transmission medium and the portion of the patient to be treated;

a window defined in the first reservoir configured to enable a camera to inspect the first reservoir for bubbles between the portion of the patient and the ultrasound transducer; and further including:

a gel pad filled with a coupling medium and positioned between the portion of the patient and the flexible membrane.

6. An ultrasonic apparatus comprising:

an ultrasonic transducer configured to produce ultrasonic waves;

a first reservoir containing a transmission medium configured to conduct the ultrasonic waves toward a portion of a patient to be treated;

a flexible membrane connected to the first reservoir disposed between the transmission medium and the portion of the patient to be treated;

a window defined in the first reservoir configured to enable a camera to inspect the first reservoir for bubbles between the portion of the patient and the ultrasound transducer; and further including: a contact surface defined between the first reservoir and a gel pad.

7. A therapeutic system comprising:

a support configured to accommodate a portion of a patient;

a first reservoir containing a transmission medium;

a flexible membrane disposed between the transmission medium and the accommodated portion of the patient;

an ultrasonic transducer configured to emit an ultrasonic beam towards the accommodated portion of the patient;

a transparent window positioned in the first reservoir opposite the accommodated portion of the patient and configured to enable inspection for bubbles between the ultrasonic transducer and the accommodated portion of the patient;

a magnetic resonance imaging apparatus configured to measure a temperature distribution in the accommodated portion of the patient and control the ultrasound transducer based on the measured temperature distribution; and further including: a gel pad filled with a coupling medium disposed between the flexible membrane and the portion of the patient and configured to transmit the ultrasound beam between the transmission medium and the portion of the patient.

* * * * *